(12) United States Patent
Kopelman

(10) Patent No.: US 9,597,165 B2
(45) Date of Patent: Mar. 21, 2017

(54) METHOD, SYSTEM AND MODEL FOR INDIRECT BONDING

(71) Applicant: ALIGN TECHNOLOGY, INC., San Jose, CA (US)

(72) Inventor: Avi Kopelman, Palo Alto, CA (US)

(73) Assignee: Align Technology, Inc., San Jose, CA (US)

( * ) Notice: Subject to any disclaimer, the term of this patent is extended or adjusted under 35 U.S.C. 154(b) by 148 days.

(21) Appl. No.: 14/567,111

(22) Filed: Dec. 11, 2014

(65) Prior Publication Data

US 2015/0093714 A1    Apr. 2, 2015

Related U.S. Application Data

(63) Continuation of application No. 12/656,960, filed on Feb. 22, 2010, now Pat. No. 8,936,464.
(Continued)

(51) Int. Cl.
*A61C 3/00* (2006.01)
*A61C 7/14* (2006.01)
(Continued)

(52) U.S. Cl.
CPC .............. *A61C 7/146* (2013.01); *A61C 7/002* (2013.01); *B29C 67/0088* (2013.01); *G05B 19/4145* (2013.01)

(58) Field of Classification Search
CPC ................................ A61C 7/146; A61C 7/002
See application file for complete search history.

(56) References Cited

U.S. PATENT DOCUMENTS 2,467,432 A    4/1949  Kesling
3,407,500 A   10/1968  Kesling
(Continued)

FOREIGN PATENT DOCUMENTS

AU    3031677 A    5/1979
AU     517102 B2   7/1981
(Continued)

OTHER PUBLICATIONS

AADR. American Association for Dental Research, Summary of Activities, Mar. 20-23, 1980, Los ngeles, CA, p. 195.
(Continued)

*Primary Examiner* — Robert N Wieland
(74) *Attorney, Agent, or Firm* — Wilson Sonsini Goodrich & Rosati

(57) ABSTRACT

A physical model of at least a portion of a patient's dentition has model dental surfaces corresponding to real dental surfaces of the patient's dentition. The physical model includes one or more targets, each configured for facilitating placement of an orthodontic appliance on the model at a desired location. The targets lack mechanical stops that are outwardly protruding from the original model dental surfaces. Also provided are a method of manufacturing a physical model for use in indirect bonding procedures, a method for indirect bonding for use in an orthodontic procedure, a method for providing an indirect bonding transfer tray for use in an orthodontic procedure, and a system for providing a physical model for use in indirect bonding orthodontic procedures.

16 Claims, 12 Drawing Sheets

Related U.S. Application Data

(60) Provisional application No. 61/202,387, filed on Feb. 24, 2009.

(51) Int. Cl.
   *A61C 7/00*    (2006.01)
   *B29C 67/00*   (2006.01)
   *G05B 19/414*  (2006.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,360,341 A | 11/1982 | Dellinger |
| 4,478,580 A | 10/1984 | Barrut |
| 4,500,294 A | 2/1985 | Lewis |
| 4,501,554 A | 2/1985 | Hickham |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,812,118 A | 3/1989 | Creekmore |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |

(56) References Cited

U.S. PATENT DOCUMENTS

| | | | |
|---|---|---|---|
| 6,398,548 | B1 | 6/2002 | Muhammad et al. |
| 6,402,707 | B1 | 6/2002 | Ernst |
| 6,482,298 | B1 | 11/2002 | Bhatnagar |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 7,020,963 | B2 | 4/2006 | Cleary et al. |
| 7,188,421 | B2 | 3/2007 | Cleary et al. |
| 7,347,688 | B2 | 3/2008 | Kopelman et al. |
| 7,404,714 | B2 | 7/2008 | Cleary et al. |
| 7,410,357 | B2 | 8/2008 | Cleary et al. |
| 7,473,096 | B2 | 1/2009 | Cinader |
| 7,762,815 | B2 | 7/2010 | Cinader et al. |
| 8,070,486 | B2 | 12/2011 | Kuperman |
| 8,235,717 | B2 | 8/2012 | Kuperman |
| 8,308,478 | B2 | 11/2012 | Primus et al. |
| 8,936,464 | B2 | 1/2015 | Kopelman |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2004/0219471 | A1 | 11/2004 | Cleary et al. |
| 2004/0219473 | A1 | 11/2004 | Cleary et al. |
| 2004/0229185 | A1 | 11/2004 | Knopp |
| 2004/0253562 | A1 | 12/2004 | Knopp |
| 2005/0055118 | A1 | 3/2005 | Nikolskiy et al. |
| 2005/0233276 | A1 | 10/2005 | Kopelman et al. |
| 2005/0244790 | A1 | 11/2005 | Kuperman |
| 2006/0001739 | A1 | 1/2006 | Babayoff |
| 2006/0084026 | A1 | 4/2006 | Cinader et al. |
| 2006/0177791 | A1 | 8/2006 | Cinader |
| 2007/0238066 | A1 | 10/2007 | Kopelman et al. |
| 2007/0275340 | A1 | 11/2007 | Kopelman et al. |
| 2007/0298364 | A1* | 12/2007 | Cinader, Jr. ............ A61C 7/146 433/3 |
| 2008/0248437 | A1* | 10/2008 | Marshall ................ A61C 7/146 433/3 |
| 2009/0220920 | A1 | 9/2009 | Primus et al. |
| 2010/0216085 | A1 | 8/2010 | Kopelman |
| 2010/0279243 | A1 | 11/2010 | Cinader et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 99/34747 A1 | 7/1999 |
| WO | WO 00/08415 A1 | 2/2000 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures, " AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/-pbourke/prolection/coords>.

Boyd et al., "Three Dimensional Diagnosis and Orthodontic Treatment of Complex Malocclusions With the Invisalipn Appliance," Semin Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

(56) References Cited

OTHER PUBLICATIONS

Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
DENTRAC Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98-Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamara, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.

(56) References Cited

OTHER PUBLICATIONS

Kamada et.al., Construction of Tooth Positioners with LTV Vinyl Silicone Rubber and Some Case Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—as Easy as One, Two, Three," AOA/Pro Corner, vol. 11, No. 1, 2 pages. (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, (Oct. 22-23, 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et a/., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee HI Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).

(56) References Cited

OTHER PUBLICATIONS

The Red, White & Blue Way to Improve Your Smile!Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

\* cited by examiner

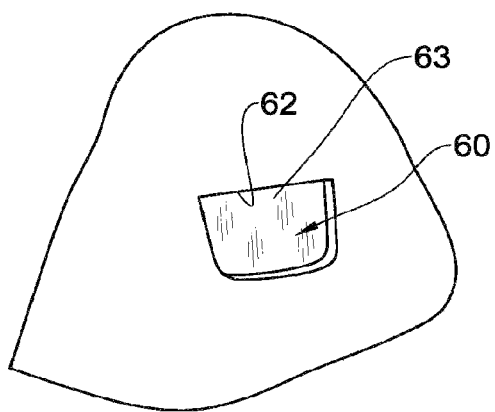
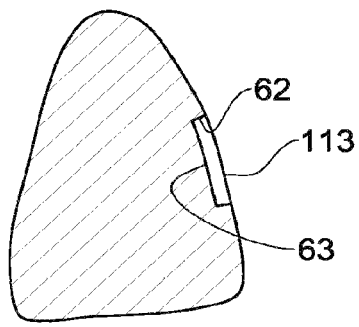
Fig. 2a Fig. 2b
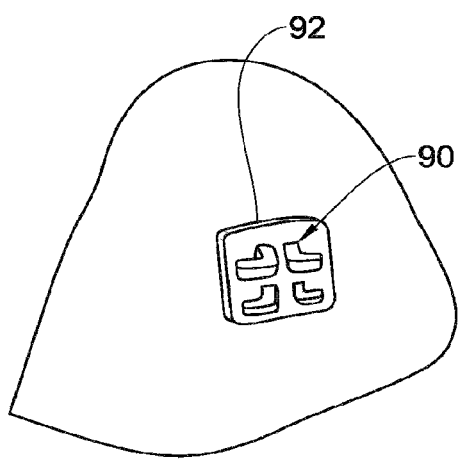
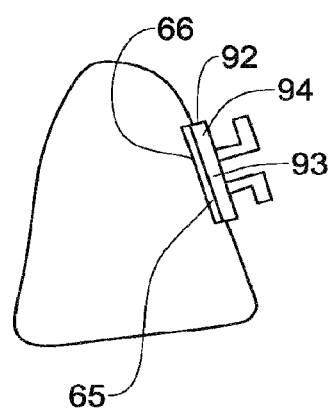
Fig. 2c Fig. 2d

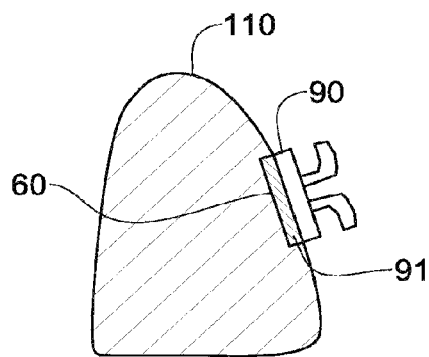
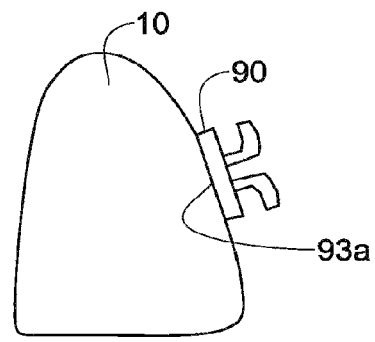
Fig. 2e          Fig. 2f
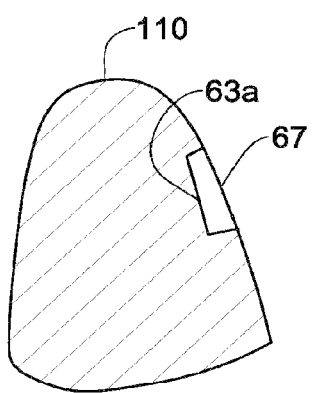
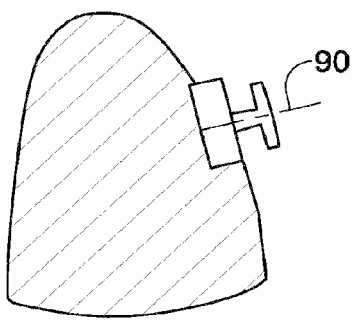
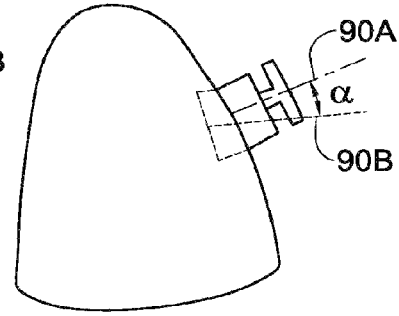
Fig. 3a          Fig. 3b          Fig. 3c

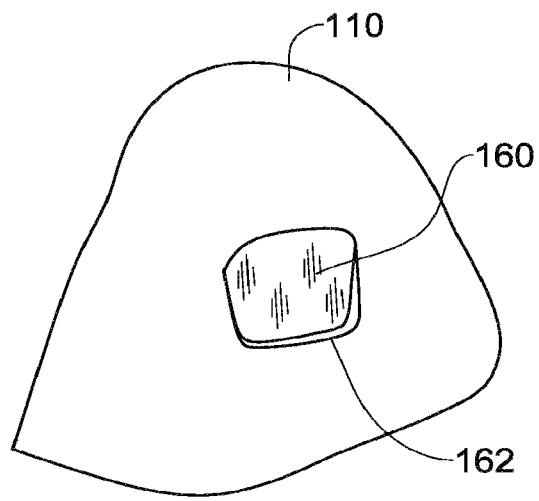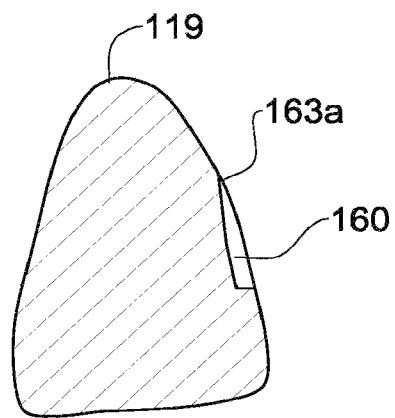
Fig. 4a Fig. 4b
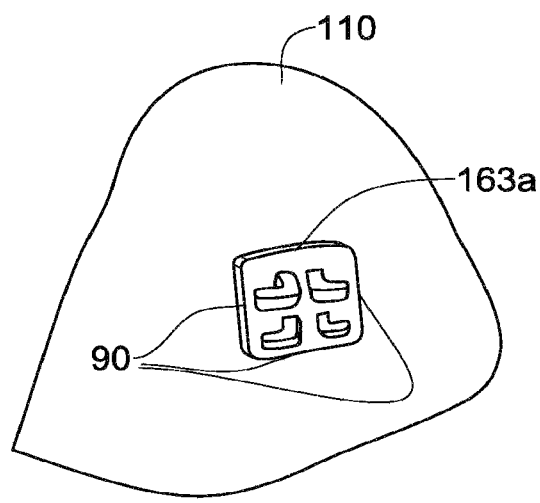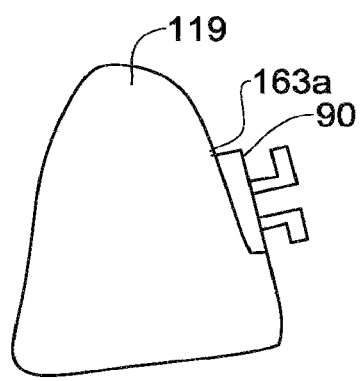
Fig. 4c Fig. 4d

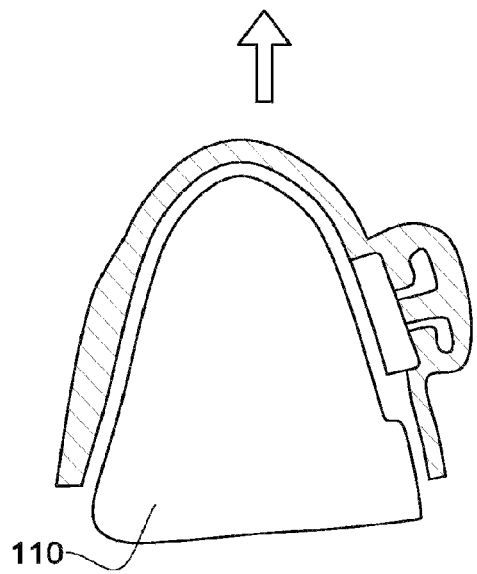
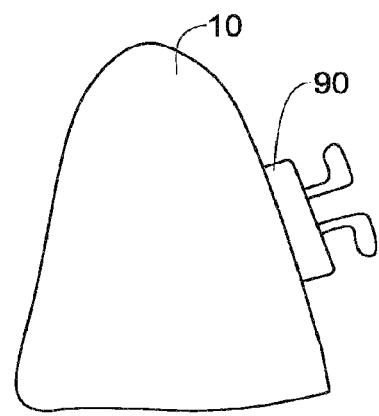
Fig. 4e    Fig. 4f
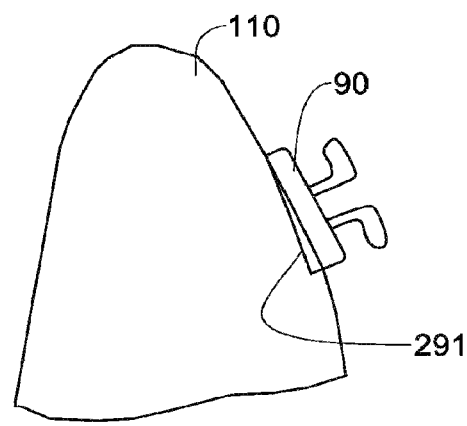
Fig. 4g

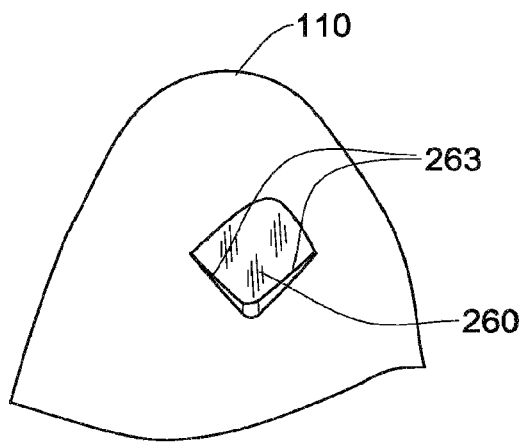
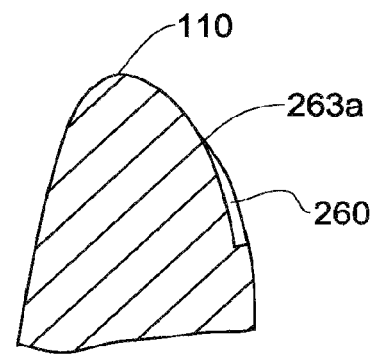
Fig. 5a　　　　　　　　　　　　　　Fig. 5b
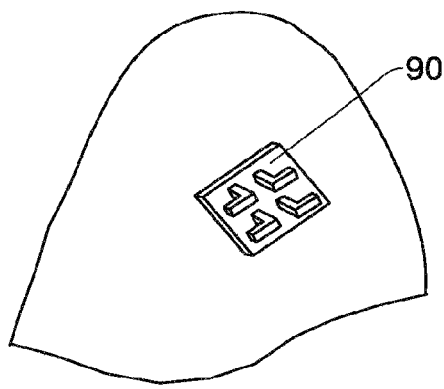
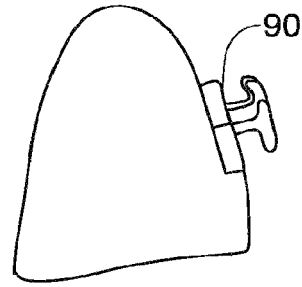
Fig. 5c　　　　　　　　　　　　　　Fig. 5d

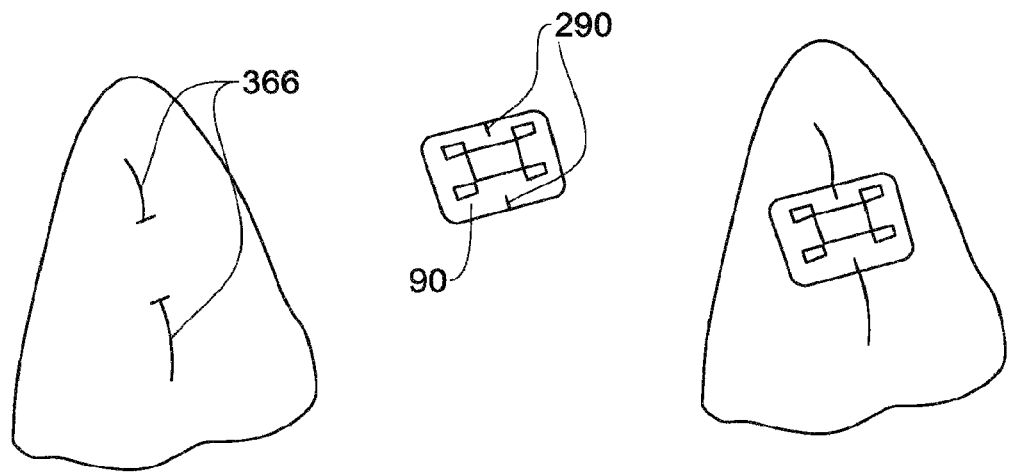
Fig. 6e                                           Fig. 6f
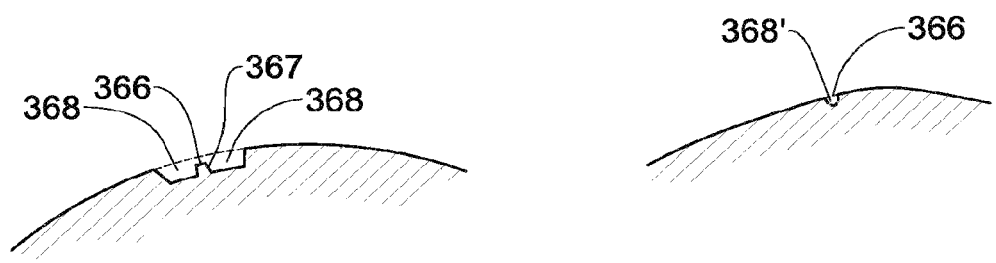
Fig. 6g                                           Fig. 6h

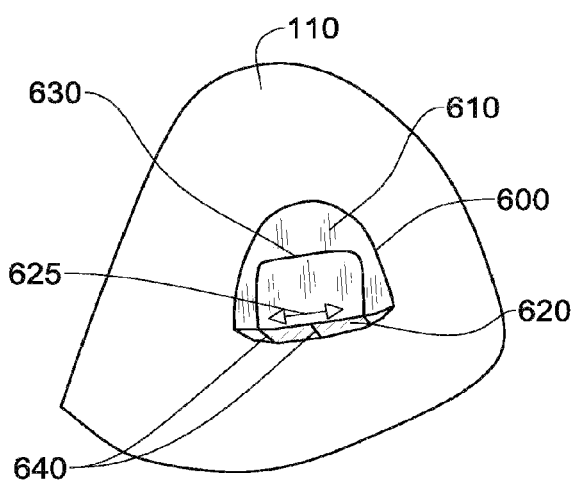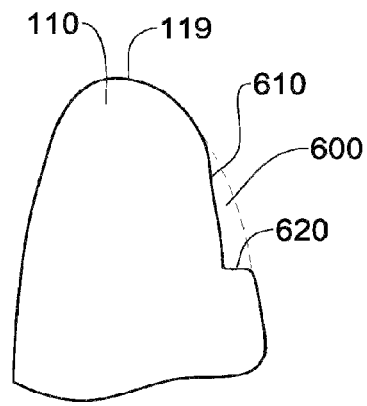
Fig. 9a　　　　　　　　　Fig. 9b
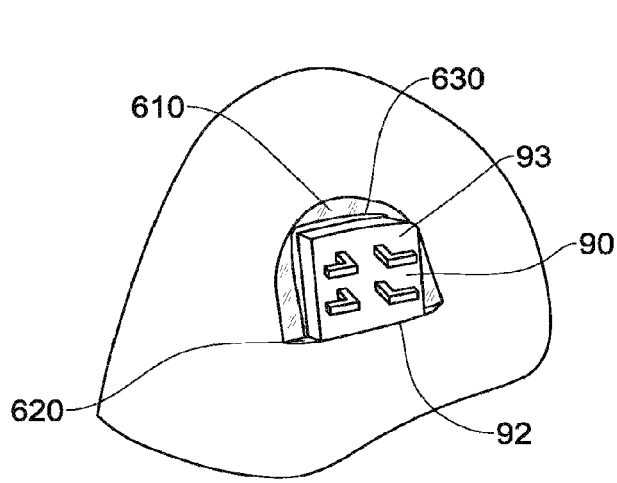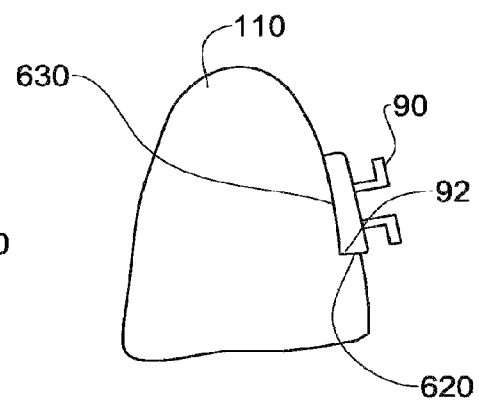
Fig. 9c　　　　　　　　　Fig. 9d

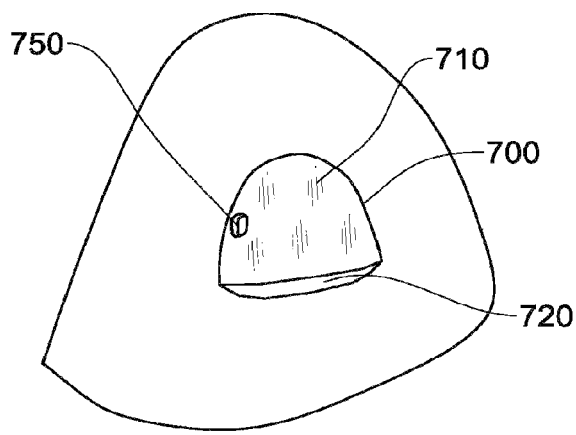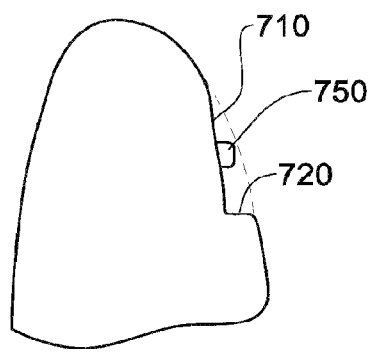
Fig. 10a  Fig. 10b
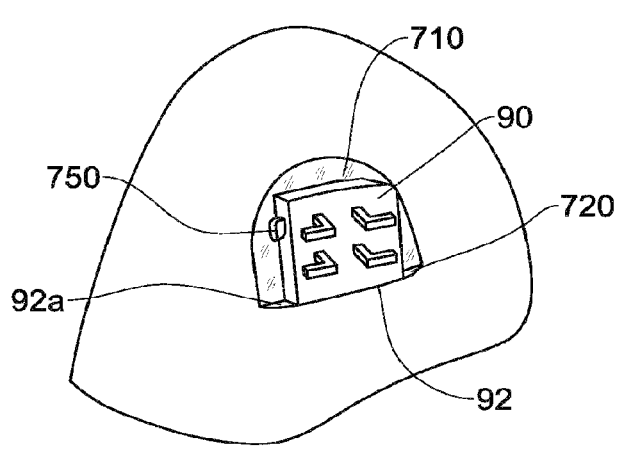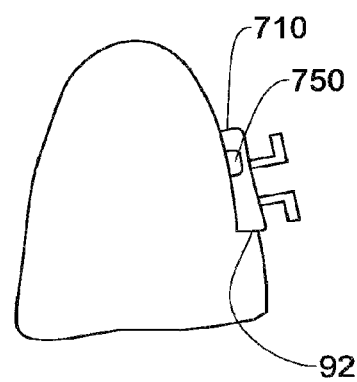
Fig. 10c  Fig. 10d

METHOD, SYSTEM AND MODEL FOR INDIRECT BONDING

CROSS-REFERENCE

This application is a continuation application of U.S. patent application Ser. No. 12/656,960, filed Feb. 22, 2010, now U.S. Pat. No. 8,936,464, issued Jan. 20, 2015, which claims benefit under 35 U.S.C. §119(e) of U.S. Provisional Patent Application No. 61/202,387, filed Feb. 24, 2009, the contents of each of which are hereby incorporated by reference in their entirety.

FIELD OF THE INVENTION

This invention relates to dental procedures, more particularly to orthodontic procedures, more particularly to methods, systems and accessories including models and transfer trays used in such procedures, and specially relating to indirect bonding procedures.

BACKGROUND OF THE INVENTION

The branch of dentistry dealing with teeth irregularities and their corrections, such as by means of braces, is known as Orthodontics. The primary purpose of orthodontic treatment is to alter the position and reorient an individual's teeth so as to modify or improve their function. Teeth may also be reoriented mainly for cosmetic reasons.

In orthodontic treatment, as currently practiced, it is often necessary to affix various orthodontic appliances to the surfaces of a patient's teeth. The location of the orthodontic appliance on the tooth as well as its orientation is a critical factor in determining the direction of movement of the teeth during the treatment, and accurate placement may ensure that the teeth are aligned with a single bracket bonding treatment. Conversely, less accurate placement of orthodontic appliances may require repeated treatments, including repeated bonding and wire bending procedures until the final alignment is achieved.

Once the position of the orthodontic appliances has been decided upon, it is thus critical that a good bond is established between the orthodontic appliances and the teeth at that position. Orthodontic appliances affixed to teeth surfaces serve to support wires and tensioning springs to exert moments of force acting to move the teeth subjected to these forces to a degree and in a direction causing the teeth to assume a desired posture in the dental arch.

In current orthodontic practice, the orthodontist decides on a general scheme of placing the orthodontic appliances on the teeth and then attaches each of them to the surface of a tooth, in an exact location and orientation previously decided. Preparatory to an orthodontic treatment, the orthodontist typically prepares a plaster model of the teeth of the treated individual and on the basis of such model, and the general scheme of placement of the orthodontic appliances can be decided.

A typical treatment plan includes, among other factors, the desired position of each of the force-inducing orthodontic implements on the teeth. The placement of the orthodontic appliances on the teeth determines the outcome of the above-mentioned movements, e.g. the degree and direction of the teeth movements. Any deviation from the planned position of the orthodontic appliances affects the outcome of the treatment. Thus, during the process of placing the orthodontic appliances on the teeth, much effort is made to ensure the accurate positioning of the orthodontic appliances in accordance with their desired position as determined by the treatment plan, and to ensure that the orthodontic appliances are properly bonded to the teeth at these positions.

The orthodontic appliances are typically placed on the buccal surface of the teeth, though at times, it is desired both from a treatment perspective as well as for reasons of external appearance of the individual, to place the orthodontic appliances on the lingual surface of the teeth.

One form of positioning brackets is known as indirect bonding, and is traditionally based on forming a tray of a thermoplastic material, or any other suitable material, over a physical model of the teeth on which the brackets have been positioned using a relatively weak adhesive, for example as described in U.S. Pat. No. 3,738,005. The brackets may be positioned onto the model in any one of a number of ways, for example as disclosed in U.S. Pat. No. 4,812,118. The tray thus comprises a negative impression of the teeth model, which is very close-fitting with respect thereto, and also has the brackets embedded in position in the tray in their correct positions with respect to the model. The tray can then be removed from the model, taking with it the brackets in the correct relative positions with respect to the negative impression. The tray is then transferred to the intraoral cavity of the patient, and when properly fitted over the appropriate arch, presents the brackets in ostensibly the correct positions vis-à-vis the teeth. It is then attempted to bond the brackets simultaneously onto the teeth, and the tray may then be removed, leaving the brackets in place.

This method is commonly practiced, and can be used for both buccal and lingual brackets. Most of the preparatory work is done by a technician rather than the dentist, and the technique results in a shorter installation time than when the brackets are installed manually one at a time, but the technician needs to have a supply of brackets readily available. This method also requires all the teeth to be dry and pre-etched, before bonding begins.

Some patent publications of general background interest include: U.S. Pat. No. 5,971,754; U.S. Pat. No. 4,360,341; U.S. Pat. No. 6,123,544; U.S. Pat. No. 4,501,554, US 2005/0244790; US 2004/0253562; US 2004/0229185.

SUMMARY OF THE INVENTION

In this specification, we shall only refer to brackets as particular examples of the orthodontic appliance (also interchangeably referred to as orthodontic element or component), to be anchored on a tooth's surface, but it is to be understood that this is only by way of example, and the invention applies to all other types of orthodontics appliances, mutatis mutandis, such as for example tubes, springs and other appliances that are configured for being affixed to a dental surface for providing an orthodontic treatment.

According to a first aspect of the invention, there is provided a physical model of at least a portion of a patient's dentition, said model comprising model dental surfaces corresponding to real dental surfaces of the patient's dentition, said physical model further comprising at least one target configured for facilitating placement of an orthodontic appliance on said model at a desired location, and wherein the or each said target lacks mechanical stops that are outwardly protruding from the said model dental surfaces.

More specifically, the or each said target lacks mechanical stops that are outwardly protruding from the said model dental surfaces and that are configured for locating the orthodontic appliance by abutment on the stops. By model dental surfaces is meant dental surfaces of real teeth that are replicated in the physical model.

According to at least some embodiments of the invention, the or each said target comprises physical and/or optical clues correlated to a respective said desired location such as to enable the respective said orthodontic appliance to be targeted onto the respective said location.

In at least some embodiments, at least one or the said target comprises a recess (interchangeably referred to herein also as a cavity and/or indentation) formed into, i.e., projecting into said model dental surface, said recess having at least one recess edge complementary to an appliance edge of a said orthodontic appliance the recess edge being configured for enabling the appliance to be received in said recess and located therein by abutment between said appliance edge and said respective recess edge.

In a variation of this embodiment, at least one or the said target comprises a recess formed into said model dental surface, said recess having at least two recess edges complementary to two appliance edges of a said orthodontic appliance to be received in said recess and located therein by abutment between said appliance edges and said respective recess edges.

In another variation of this embodiment, at least one or the said target comprises a recess formed into said model dental surface, said recess having at least three recess edges complementary to three appliance edges of a said orthodontic appliance to be received in said recess and located therein by abutment between said appliance edges and said respective recess edges.

In another variation of this embodiment, at least one or the said target comprises a recess formed into said model dental surface, said recess having a plurality of recess edges complementary to the appliance edges of a said orthodontic appliance to be received in said recess and located therein by abutment between said appliance edges and said respective recess edges. For example, the appliance may have four edges, and the recess also has four complementary edges.

In another embodiment, at least one or the said target comprises a physical marking or visual marking formed on said model dental surface, said marking providing sufficient visual clues to enable said orthodontic appliance to be located at the desired location on the model dental surface. For example, the physical marking may comprise a mark or symbol indented, engraved or otherwise formed projecting into said model dental surface (for example as a mild depression) having sufficient visual targeting information to enable a user to navigate a respective said orthodontic appliance and targeted the same onto a desired location on said model. In another example, the visual marking may comprise a mark or symbol having an optical characteristic different from an optical characteristic of a remainder of said model dental surface not comprising said target, and having sufficient visual targeting information to enable a respective said orthodontic appliance to be targeted to a desired location on said model; the optical characteristic may include, for example, at least one of color and contrast. The markings may be inscribed, printed or otherwise formed in the model, and help to visually align the orthodontic appliance at the desired position, without the need for physical stops to keep it in place.

The targets, in particular the recesses and/or markings may be made by CNC machining the physical model, for example, during manufacture of the model or after manufacture of the model. Alternatively, other material removal manufacturing processes may be used for manufacturing the model and targets. Alternatively, other methods may be used for manufacturing the model and targets, for example rapid prototyping techniques. Optical markings may be provided on the physical model by means of computer controlled printing, drawing or other methods that leave a mark or symbol on the model.

The physical marking or visual marking may be configured for enabling a datum mark on said appliance to be aligned therewith such as to locate the appliance at the desired position on the model.

In any particular application of the invention, a plurality of targets may be provided on a corresponding plurality of model teeth of a physical model, according to the requirements of a treatment plan, and the targets may include any combination or permutation of different types of targets— for example a mix between targets that provide a recessed mechanical stop for physically anchoring the respective appliance on the tooth model (the same type of mechanical stop, or different types of mechanical stops), and targets in the form of optical markings that only provide an optical guide (but no anchoring stops) to enable the appliance to be navigated and targeted into the desired place (the same or different types of optical markings). Alternatively, the same type of target may be provided throughout the model. In at least some applications, at least one target may include both a recessed mechanical stop and an optical marking for targeting.

According to a second aspect of the invention, there is provided a method of manufacturing a physical model for use in indirect bonding procedures, comprising:

(a) providing a physical model of at least a portion of the intra oral cavity of a patient;

(b) determining desired positions of orthodontic appliances with respect to said intra oral cavity to enable an orthodontic procedure to be carried out;

(c) providing at least one target on the physical model, the or each said target being configured for facilitating placement of said orthodontic appliance on said physical model at a desired location, and wherein the or each said target lacks mechanical stops that are outwardly protruding from the said model dental surfaces.

The positions in step (b) may be determined with respect to a virtual model corresponding to the physical model of step (a).

Step (c) may be carried out by means of a computer controlled manufacturing process, including, for example, at least one of a CNC machining process and a rapid prototyping manufacturing process.

In at least some embodiments, step (c) is performed concurrently while manufacturing the physical model in step (a).

The physical model may contain one or more characteristic and features of the physical model as per the first aspect of the invention, mutatis mutandis.

According to a third aspect of the invention there is provided a method for indirect bonding for use in an orthodontic procedure, comprising:

(a) providing a physical model of at least a part the intra oral cavity of a patient, said physical model comprising at least one target, the or each said target being configured for facilitating placement of said orthodontic appliance on said physical model at a desired location for enabling said orthodontic procedure, and wherein the or each said target lacks mechanical stops that are outwardly protruding from the said model dental surfaces;

(b) using the targets, locating the orthodontic appliances at respective said desired positions on said physical model;

(c) providing a transfer tray over said physical model such as to anchor said orthodontic appliances within said transfer tray;

(d) transferring the orthodontic appliances to the real intra-oral cavity of the patient.

The physical model may contain one or more characteristic and features of the physical model as per the first aspect of the invention.

According to a fourth aspect of the invention, there is provided a method for providing an indirect bonding transfer tray for use in an orthodontic procedure, comprising:

(a) providing a physical model of at least a part the intra oral cavity of a patient, said physical model comprising at least one target, the or each said target being configured for facilitating placement of said orthodontic appliance on said physical model at a desired location for enabling said orthodontic procedure, and wherein the or each said target lacks mechanical stops that are outwardly protruding from the said model dental surfaces;

(b) using the targets, locating the orthodontic appliances at respective said desired positions on said physical model;

(c) producing a transfer tray over said physical model such as to anchor said orthodontic appliances within said transfer tray;

(d) removing the transfer tray, with the orthodontic appliances in situ therein, from the physical model.

The physical model according to the fourth aspect of the invention may have one or more characteristic and features of the physical model as per the first aspect of the invention, mutatis mutandis.

According to a fifth aspect of the invention, there is provided a system for providing a physical model for use in indirect bonding orthodontic procedures, comprising a computer controlled manufacturing center configured for producing, on a physical model of at least part of the intra-oral cavity of a patient, at least one target, the or each said target being configured for facilitating placement of an orthodontic appliance on said physical model at a desired location for enabling an orthodontic procedure to be carried out on the patient, and wherein the or each said target lacks mechanical stops that are outwardly protruding from the said model dental surfaces.

The physical model according to the fifth aspect of the invention may have one or more characteristic and features of the physical model as per the first aspect of the invention, mutatis mutandis.

Thus, according to at least some aspects of the invention, a physical model of at least a portion of a patient's dentition has model dental surfaces corresponding to real dental surfaces of the patient's dentition. The physical model includes one or more targets, each configured for facilitating placement of an orthodontic appliance on the model at a desired location. The targets lack mechanical stops that are outwardly protruding from the original model dental surfaces. Also provided are a method of manufacturing a physical model for use in indirect bonding procedures, a method for indirect bonding for use in an orthodontic procedure, a method for providing an indirect bonding transfer tray for use in an orthodontic procedure, and a system for providing a physical model for use in indirect bonding orthodontic procedures.

One feature of at least some embodiments and aspects of the invention is that the 5 targets may be retrofittably provided in existing physical models, as the targets are marked on the model or recesses provided into the surface of the model.

Another feature of at least some embodiments and aspects of the invention is that the physical model can be easily repaired if damaged, or if a different position is required. For example, an existing recess can be filled in and re-machined, or an existing marking can be erased or covered over and redrawn.

Another feature of at least some embodiments and aspects of the invention is that the exact location in all degrees of freedom of an orthodontic appliance on a real tooth can be exactly repeated in a tooth model, by providing where necessary buffer layer between the model and the appliance.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2a to 2f show various views of a tooth model portion of the physical model of FIG. 1, including a target according to a first embodiment of the invention: FIGS. 2a, 2b illustrate the target on the tooth model in isometric and cross-sectional view, respectively; FIGS. 2c, 2d illustrate the orthodontic appliance in situ on the target on the tooth model in isometric and cross-sectional view, respectively; FIGS. 2e, 2f illustrate in side view, a variation of the embodiment of FIGS. 2a to 2d, the orthodontic appliance mounted to the tooth model via a buffer layer and the orthodontic appliance mounted to the real tooth without the buffer, respectively.

FIGS. 3a to 3c show in a variation of the embodiment of FIGS. 2a to 2f; FIG. 3a illustrates a cross-section of the tooth model showing the shape of the recess; FIG. 3b illustrates a cross-section of the tooth model showing the orthodontic appliance mounted in the recess; FIG. 3c illustrates a side view of the real tooth showing the corresponding change in angular position of the orthodontic appliance relative to its position in FIG. 3b.

FIGS. 4a to 4g show various views of another variation of the embodiment of FIGS. 2a to 2f: FIGS. 4a, 4b illustrate the target on the tooth model in isometric and cross-sectional view, respectively; FIGS. 4c, 4d illustrate the orthodontic appliance in situ on the target on the tooth model in isometric and cross-sectional view, respectively; FIGS. 4e, 4f illustrate in side view the orthodontic appliance captured in the transfer tray and being removed from the tooth model, and the orthodontic appliance mounted to the real tooth, respectively; FIG. 4g illustrates in side view, a variation of the embodiment of FIGS. 4a to 4f, in which the orthodontic appliance is mounted to the tooth model via a buffer layer.

FIGS. 5a to 5d show various views of another variation of the embodiment of FIGS. 2a to 2f: FIGS. 5a, 5b illustrate the target on the tooth model in isometric and cross-sectional view, respectively; FIGS. 5c, 5d illustrate the orthodontic appliance in situ on the target on the tooth model in isometric and cross-sectional view, respectively.

FIGS. 6a to 6h show various views of a second embodiment of the invention and variations thereof: FIGS. 6a, 6b illustrate the target on the tooth model in isometric and cross-sectional view, respectively; FIGS. 6c, 6d illustrate variations of the embodiment of FIGS. 6a and 6b; FIGS. 6e and 6f show yet another variation of the embodiment of FIGS. 6a and 6b; FIGS. 6g and 6h illustrate examples of cross-sections of the embodiments of the targeting marks of FIGS. 6a to 6f.

FIGS. 9a to 9d show various views of a third embodiment of the invention: FIGS. 9a, 9b illustrate the target on the tooth model in isometric and cross-sectional view, respectively; FIGS. 9c, 9d illustrate the orthodontic appliance in situ on the target on the tooth model in isometric and cross-sectional view, respectively.

FIGS. 10a to 10d show various views of another variation of the embodiment of FIGS. 9a to 9d: FIGS. 10a, 10b illustrate the target on the tooth model in isometric and cross-sectional view, respectively; FIGS. 10c, 10d illustrate the orthodontic appliance in situ on the target on the tooth model in isometric and cross-sectional view, respectively.

DETAILED DESCRIPTION OF THE INVENTION

Figure 1:
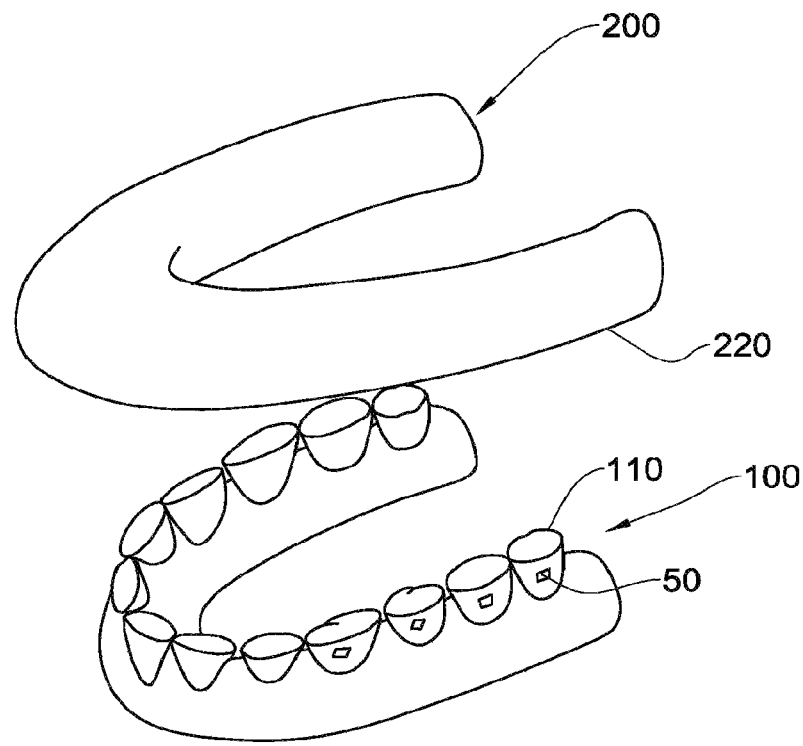
FIG. 1 is an isometric exploded view of a physical model and transfer tray according to embodiments of the invention.

Referring to FIG. 1, a first embodiment of the present invention comprises a physical model of a tooth arch, generally designated with numeral 100, comprising a plurality of dental appliance targets 50, also referred to interchangeably herein as targets 50.

In this embodiment, the model 100 is a physical replica, made from a suitable material as is known in the art, representing the real tooth arch of a patient regarding which it is desired to provide an orthodontic treatment to at least some of the teeth therein. In alternative variations of this embodiment, the model may instead be a physical replica of part of an arch, for example representing a number of teeth or even representing one tooth of the dentition of the patient.

Figure 1A:
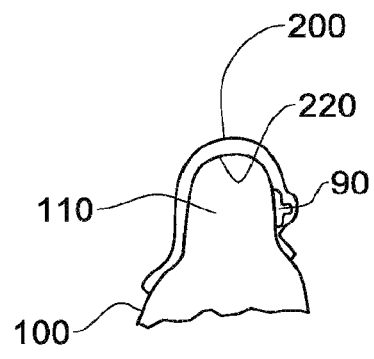
FIG. 1a shows a cross-sectional view of the model and tray of FIG. 1, taken at a position comprising an orthodontic appliance.
Figure 1B:
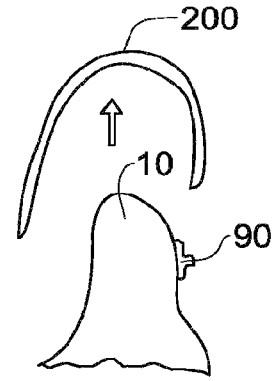
FIG. 1b shows a cross-sectional view of the real tooth corresponding to the model of FIG. 1b and comprising an orthodontic appliance, with the tray being removed.

One or more than one target 50 is provided on the representation of a respective tooth model 110 in the model 100, each at a position relative to the dental surfaces of the respective tooth model 110 that is considered to provide the required orthodontic treatment for the patient when the respective orthodontic appliance 90 is placed on the corresponding position real dental surface of the real respective tooth 10 of the patient (FIGS. 1a, 1b). It is also to be noted that the model dental surfaces of the physical model referred to herein are external model surfaces that correspond only to the respective real dental surfaces of the real teeth, and thus do not include recesses, indentations or other modifications formed in the model and that penetrate the original dental surface of the model, wherein such recesses, indentations or other modifications do not have a physical counterpart in the real dental surfaces.

Each target 50 is configured for facilitating placement of the respective orthodontic appliance 90 on the model 100, by providing visual clues and/or mechanical stops, in particular recessed mechanical stops, for aligning the orthodontic appliance 90 accurately on the respective tooth surface.

Once the orthodontic appliances 90 are affixed on the model 100 at the desired positions over the respective tooth representations 110, a transfer tray 200 is provided to fit over the model 100. The inside shape of each of the cavities 220 of the tray 200 is formed to be substantially complementary to the external shape of the particular model tooth of the model 100 that is received therein, in particular the lingual and buccal/labial surfaces of the model teeth. The tray 200 is also designed to embed or fix the orthodontic appliances 90 into the tray material at their correct positions relative thereto (FIG. 1a), and when fixed thus, the tray 200, together with the orthodontic appliances 90 can then be removed from the model 100 and transferred to the real arch of the patient to enable fixation of the orthodontic appliances 90 to the real teeth in an indirect bonding procedure, after which the tray 200 is removed (FIG. 1b), as is known per se in the art.

Thus, the targets 50 are configured for enabling each of the orthodontic appliances 90, for example brackets, to be properly positioned with respect to the respective teeth models 110 that they are to be temporarily bonded to, and at least serve as a navigational and positional guide for the placement of the orthodontic appliances 90 onto the desired positions on model 100.

Referring to FIGS. 2a to 2f, in one embodiment, the target 50 for a respective tooth model 110 is in the form of a recessed mechanical stop, and comprises a cavity or recess 60 indented or otherwise projecting into the surface 115 of the tooth model 110, and appropriately shaped to enable an orthodontic appliance 90 to be mechanically received therein. In particular, the recess 60 is defined by a rectangular planform with four inward facing edges 62 that are complementary to and correspond to the four outer edges 92 of the base element 94 of an orthodontic appliance 90, and which circumscribe a base 63 of the recess 60. The edges 62 of the recess 60 have a plan shape substantially complementary to the plan shape of the part of the appliance 90 that is to be in abutting contact with the real tooth, and thus define the location of the edges 92 of the base 93 of orthodontic appliance 90, which can then be placed in the desired location on the respective tooth model 110 by simply inserting the base 93 in the recess 60, for later transfer to the real tooth via the transfer tray 200. Typically, the tooth model 110 is solid or at least has a thickness in the region of the recess 60 such that the abutment surface 93a (FIG. 2f) of the base 93 can be in abutment with the model material, directly or indirectly via a buffer layer.

In the embodiment of FIGS. 2a to 2f, the shape of abutment surface 93a (FIG. 2f) of the base 93 essentially follows the contour of the original tooth surface portion 113 of the tooth model 110 that is now missing on account of the recess 60 (FIG. 2b), but is generally uniformly linearly displaced inwardly into the tooth model 110 with respect to the contour of the missing tooth surface portion 113, for example in an orthogonal direction with respect thereto. In this manner, when an initially flowable buffer material layer 65, such as an adhesive, is placed between the appliance base 93 and the recess base 63, once the layer 65 sets and solidifies, the abutment surface 66 of the layer 65 has a shape complementary to that of recess base 63, and thus also of the original tooth surface 113 "above" the recess base 63. This enables the orthodontic appliance 90, together with the shaped layer 65, to sit in close fitting abutment over the tooth surface of the respective real tooth 10 after the orthodontic appliance 90 is transferred thereto via the tray 200.

Thus, the recess 60 has a nominally uniform depth with respect to the model tooth surface which can be of the same order as the thickness of the base 94, for example, or alternatively more, or alternatively less, but sufficient to enable the orthodontic appliance 90 to be positively located in the recess by the user, without the need for special tools other than optionally a holder for manipulating the orthodontic appliance 90 into engagement with the recess 60.

The recess 60 may be formed on the buccal/labial side, or on the lingual side, or one recess 60 may be provided at each of both sides of the tooth 110 of model 100, as required. In particular, and referring to FIGS. 2a and 2c, the recess 60 is of a shape and size substantially complementary to the shape and size of the desired respective orthodontic appliance 90 that is to be fitted there into via base 93.

In operation, the appliance 90 is manually maneuvered into place by the user, and fixed in place in the recess 60, for example by means of a weak adhesive, and the transfer tray 200 is formed over the model 100 including the appliance 90. Alternatively, in some cases the orthodontic appliance 90 may have an interference fit with respect to the recess 60, and thus is held in place therein without the need for use of an adhesive. In any case, once the orthodontic appliance 90 is engaged in the recess 60 and the tray formed over the model 100 and the orthodontic appliance 90, the tray 200 together with the orthodontic appliance 90 in situ is removed from the model 100, and transferred to the intra-oral cavity of the patient, such that the orthodontic appliance 90 is bonded to the respective real tooth of the patient. The above procedure is of course applicable to one or to a plurality of orthodontic appliances 90 that are transferred via the tray 200.

In this embodiment, the appliance 90 sits substantially on the same location and orientation along the surface of the real tooth as in the tooth model 110, but on the surface of the real tooth rather than below the tooth surface, in contrast with the position of the orthodontic appliance 90 with respect to the model tooth 110, in which the orthodontic appliance 90 was accommodated in recess 60, below the model tooth surface. Since the orthodontic appliance 90 is fully constrained in all six degrees of freedom by the tray 200, the orthodontic appliance 90 is made to abut the respective tooth by making use of the elasticity of the tray and manually pressing the orthodontic appliance 90 towards the respective tooth. The elasticity of the tray 200 also assists in enabling the orthodontic appliances 90 to be extracted from their respective recesses 60 in the model 100 when removing the tray 200 from the model 100.

In an alternative variation of this embodiment, and referring to FIGS. 2e and 2f in particular, the orthodontic appliance 90 may be fitted with a buffer layer 91 that is designed to have the same thickness as the depth of recess 60. Thus, when the orthodontic appliance 90 with the buffer layer 91 is implanted in the recess 60, the full height of the orthodontic appliance 90 stands above the surface of the model tooth 110. For example, the buffer layer 91 may comprise a piece of sheet material of the desired thickness, and cut to have the same planform as the base 93, or such as to have a planform that is enclosed within the edges 92. When the transfer tray 200 is placed over the model 100 and the orthodontic appliance 90, this is removed from the respective tooth model 110, and the buffer layer 91 may be removed from the appliance 90 at the same time or at a later time prior to attachment of the appliance to the real tooth 10. Thus, when the transfer tray 200 places the orthodontic appliance 90 on the real tooth 10, the orthodontic appliance 90 is at the same position in all degrees of freedom with respect to the real tooth 10 as it was with respect to the tooth model 110.

In yet another variation of the embodiment of FIG. 2e, the buffer layer 91 may be made of a magnetized or magnetizable material, and may be mounted in the recess 60, optionally permanently, for example by bonding. Location and placement of this magnetized buffer layer is facilitated by having the plan shape of the buffer layer substantially complementary to that of the recess 60, similar to placement of the orthodontic appliance 90 in recess 60 according to the embodiment of FIGS. 2a to 2d, mutatis mutandis. Then, the orthodontic appliance 90, which at least for this case is made from a magnetic or magnetizable material or comprises a magnetic or magnetizable material at least at the base 94 thereof, is located over the magnetized buffer layer 91 by means of the magnetic attraction there between. In use, the tray 200 is formed over the orthodontic appliance 90, which is transferred to the real tooth, as before.

In alternative variations of the embodiment of FIGS. 2a to 2f, and referring to FIGS. 3a to 3c for example, the recess base 63a may be inclined in any suitable manner with respect to the original surface profile 67 of the tooth model 110 directly above the recess 60, according to the desired inclination of the orthodontic appliance 90 with respect to the tooth surface. For example, a desired level of torque and/or tip and/or rotation angles may be provided on the real tooth surface (FIG. 3c) by suitably varying the depth(s) of one or more of the edges 62 of the recess 60 (FIGS. 3a, 3b), in a suitable manner such as to incline the recess base 63a. Thus, as illustrated in FIGS. 3a to 3c, the orientation of the appliance 90 with respect to the surface of the real tooth 10, as symbolized by an imaginary datum line 90A orthogonal to the surface, is inclined by an angle a with respect to the inclination of the appliance with respect to its position on the tooth model 110 (datum line 90B).

In an alternative variation of this embodiment, and referring to FIGS. 4a to 4f, the target 50 may be in the form of a wedge-shaped recess 160, having three edges 162 in the shape of a U against which the desired bracket or other orthodontic appliance 90 can be abutted by means of three edges 92 thereof to positively fix the position of the orthodontic appliance 90 with respect to the respective tooth model 110. Thus, the recess 160 lacks a fourth recessed edge at the opening 163a of the U in the occlusal direction towards the apex 119 of the tooth model 110. As best seen in FIG. 4e, the lack of a recessed edge at opening 163a facilitates removal of the tray 200 together with the orthodontic appliance 90, as the tray 200 is essentially lifted away from the tooth model 110 in the direction of the opening, i.e., in the occlusal direction, and there is no resistance offered by the recess 160 to movement of the orthodontic appliance 90 in this direction. When transferred to the real tooth 10 (FIG. 4l), the appliance 90 sits substantially on the same location and orientation along the surface of the tooth 10 as in the model 110, but in relative terms the appliance is slightly tilted on the surface of the real tooth 10 with respect to its original position relative to the tooth model 110.

Optionally, and referring to FIG. 4g, the orthodontic appliance 90 may be fitted with a buffer layer 291 that is designed to have the same cross-section as that of recess 260, i.e. the wedge-shaped variable thickness as the depth of recess 260, so that when the orthodontic appliance 90 with the buffer layer 291 is implanted in the recess 260, the full height of the orthodontic appliance 90 stands above the surface of the model tooth 110. When the transfer tray 200 is placed over the orthodontic appliance 90, this is removed from the model 110, and the buffer layer 291 is removed at the same time or later. Thus, when the transfer tray 200 places the orthodontic appliance 90 on the real tooth, the orthodontic appliance 90 is at the same, correct position in all degrees of freedom, with respect to the real tooth 10 as it was with respect to the tooth model 110. Otherwise, the embodiment of FIGS. 4a to 4g is substantially similar to that of FIGS. 2a to 2f and 3a to 3c, mutatis mutandis.

In an alternative variation of the embodiment of FIGS. 4a to 4g, and referring to FIGS. 5a to 5d, the target 50 is also in the form of an open recess 260, but this is a V-shaped recess having only two adjoining edges 263 against which the desired bracket or other orthodontic appliance 90 can be abutted to positively fix the position of the bracket with respect to the model 100. In a similar manner to the embodiment of FIGS. 4a to 4g, mutatis mutandis, the lack of a recessed edge at opening 263a of the "V" facilitates removal of the tray 200 together with the orthodontic appliance 90, as the tray is essentially lifted away from the tooth model 110 in the direction of the opening, and there is no resistance offered by the recess 260 in this direction. Also similarly, mutatis mutandis, when transferred to the real tooth, the appliance 90 sits substantially on the same location and orientation along the surface of the real tooth as in the model 110, but in relative terms the appliance may be slightly tilted on the surface of the real tooth with respect to its position in the model 110, though optionally a buffer layer similar to that of FIG. 4g, mutatis mutandis, may be used with the embodiment of FIGS. 5a to 5d to enable the orthodontic appliance 90 to be oriented on the model 110 in the exact manner that it is wished to place the orthodontic appliance on the real tooth.

The targets 50 in the form of recesses 60, 160 or 260 can be formed on the tooth model 100, for example as follows.

The location and orientation of the targets 50 for each real tooth are first identified, according to a set up plan provided by the orthodontist, as the respective locations and orientations appropriate for bonding or otherwise fixing the brackets or other orthodontic appliances onto the misaligned teeth of the arch such that the teeth may be aligned in the manner desired in response to the orthodontic treatment.

Figure 7:
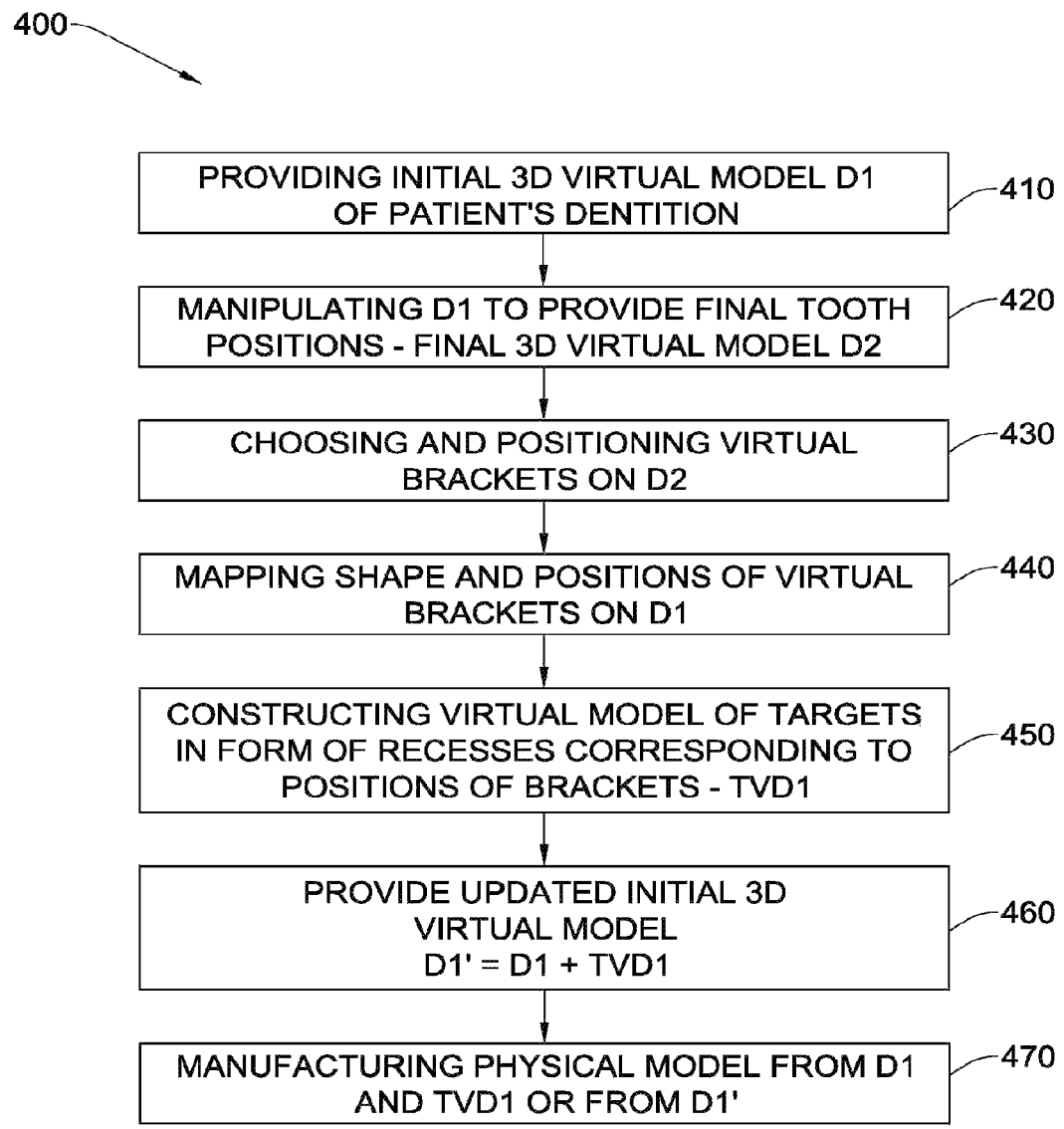
FIG. 7 illustrates general steps of a method for manufacturing the tooth model of FIG. 1 according to an embodiment of the invention.

According to an aspect of the invention, and referring to FIG. 7, a 3D numerical model of the teeth of the patient is provided, and the three-dimensional positions of the brackets or other orthodontic appliances with respect to the 3D numerical model are defined, according to method 400.

For example, in step 410, the three dimensional (3D) structure of the patient's dentition, including the teeth that are required to be moved during the course of the orthodontic treatment, and preferably the full dentition of the arch on which these teeth are located, is determined, and provided in digitized form, hereinafter referred to as the initial 3D digitized model or virtual model of the dentition, D1. Optionally the three dimensional (3D) structure of both arches is provided.

The 3D digitized dental model D1 may be obtained in any number of ways. For example, the intra-oral cavity may be scanned or imaged using technology known in the art, including X-rays, CT, MRI, using direct contact methods or using non-contact methods such as for example those that employ an optical probe scanner. For example, such a scanner may comprise a probe for determining three dimensional structure by confocal focusing of an array of light beams, for example as marketed under the name of iTero or as disclosed in WO 00/08415, the contents of which are incorporated herein in their entirety. Alternatively, the required scanning may be accomplished using any suitable scanning apparatus for example comprising a hand held probe. Optionally, color data of the intraoral cavity may also provided together with the 3D data, and thus the first virtual model 500 comprises spatial and color information of the dental surfaces scanned. Examples of such scanners are disclosed in US 2006-0001739, and which is assigned to the present Assignee. The contents of the aforesaid co-pending application are incorporated herein by reference in their entirety. Alternatively, an impression (negative casting) of a patient's teeth is obtained in a manner well known in the art, and this is used for preparing a positive cast suitable for scanning or imaging. Alternatively, the negative casting itself is scanned or imaged. Alternatively, a composite positive-negative model may be manufactured and processed to obtain 3D digitized data, for example as disclosed in U.S. Pat. No. 6,099,314, assigned to the present Assignee, and the contents of which are incorporated herein in their entirety. In any case, the 3D virtual model D1 may be associated with a complete dentition, or with a partial dentition, comprising the teeth that are to be treated.

Providing a digitized data set corresponding to the virtual model D1 from such scanning or imaging is also known in the art and will not be described further. The digitized data set of virtual model D1 is manipulable by means of a computer, and thus allows the next step to be performed using a suitable computer.

In the next step 420, computer based methods are used for generating the set up, and the virtual model D1 is manipulated to provide a final tooth arrangement comprising a final digitized data set corresponding to a final 3D virtual model D2, in which each virtual tooth is positioned in the desired position, for example as disclosed in WO 99/34747 or in U.S. Pat. No. 5,975,893, the contents of which are incorporated herein in their entirety. Essentially, the 3D digitized data corresponding to the individual teeth of the initial virtual model D1 are separated from one another, and the user repositions the 3D individual tooth data for each tooth based on visual appearance, and/or using rules or algorithms, and/or according to prescriptions provided by the orthodontist, to provide the final virtual model D2.

In the next step 430, and based on the final data set corresponding to virtual model D2, brackets or other orthodontic appliances are chosen and "virtually" positioned within the computer environment, i.e. by means of the computer, on the aligned teeth virtual model D2, and the corresponding positions of the brackets or other orthodontic appliances are then mapped back to the initial virtual model D1 in step 440. The position and orientation of the brackets or other orthodontic appliances can then be incorporated into the initial virtual model D1, and virtual artifacts which correspond to the shape of the recess 60, 160 or 260 that is chosen for each particular target 50, collectively referred to herein as target virtual model TVD1, are created in step 450, and may be added to virtual model D1 to provide modified virtual model D1' in step 460, which includes the original virtual model D1 modified to integrally include the chosen recesses 60, 160 or 260 in the positions corresponding to the chosen respective orthodontic appliances 90 instead of the original virtual tooth surfaces at those positions.

In alternative variations of this embodiment, the position and orientation of the brackets or other orthodontic appliances are provided in a different manner—for example manually, or by directly interacting with model D1 to choose each position and orientation using the practitioner's skill and experience. The positions and orientations can then be incorporated into the initial virtual model D1, and virtual artifacts which correspond to the shape of the recess 60, 160 or 260 that is chosen for each particular target 50, collectively referred to herein as target virtual model TVD1, are created in step 450, and may be added to virtual model D1 to provide modified virtual model D1' in step 460.

The physical model is then manufactured in step 470 based on the virtual models D1 and TVD1, or based on the virtual model D1, using computer controlled manufacturing methods.

For example, the model 100 may be manufactured using material removal techniques, for example CNC machining methods, or other methods, such as for example rapid prototyping techniques.

Using CNC machining methods, the model 100 may be produced either indirectly or directly. Such indirect methods may comprise, e.g., manufacturing an appropriate female mold using CNC techniques, and then producing a model 100 from the mold. The female mold comprises an internal 3D structure substantially complementary to that defined by virtual model D1'.

In direct CNC machining methods, a suitable CNC machine may be programmed to provide material removal passes over a blank of suitable material, based on dataset D1 or D1', such as to manufacture the model 100. For example, the targets 50 may be integrally formed with the model 100, wherein the model 100 is manufactured based on virtual model D1'. Alternatively, the targets 50 may be formed as a separate machining operation after the model 100 is produced based on virtual model D1, wherein the position and form of the targets 50 is post-machined based on target virtual model TVD1.

Alternatively, the model 100 may be formed using other techniques such as for example from an impression of the intra-oral cavity, and the targets 50 may be subsequently formed on such a physical model using CNC machining techniques based on target virtual model TVD1. In such a case, the spatial position and orientation of model 100 as a whole must be known with respect to a machining datum so that CNC machining operations are applied to the desired parts of the model to form the recesses 60, 160 and/or 260. Accordingly, it is possible to set the model 100 on a rig or chuck to hold the same in place, and thereafter scanned using a suitable 3D scanner to provide a 3D virtual model, nominally equivalent to model D1, to be followed by machining of the recessed based on target virtual model TVD1, which is manipulated to be in registry with the virtual model of the scanned physical model 100. Alternatively, the model 100 may be fabricated with indicia that help align the model 100 with respect to predetermined datums in the CNC machine, to which the target virtual model TVD1 is also referenced.

Alternatively, the model 100 may be fabricated using other methods. For example, the model 100 may be fabricated using rapid prototyping techniques, for example based on a stereolithography machine, such as for example Model SLA-250/50 available from 3D System, Valencia, Calif., based on the virtual model D1. A liquid or non-hardened resin is hardened into a 3D form that can be separated from the non-hardened liquid or resin to form a positive model 100 from the 3D numerical model D1 thereof. Then, the targets 50 may be formed in the model 100 in a similar manner to that described above, for example, mutatis mutandis, for example by CNC machining. Alternatively, the model 100 may be manufactured integrally with the targets 50 using rapid prototyping techniques in a similar manner to that described herein, mutatis mutandis, based on virtual model D1'.

Once the physical tooth model 100 is manufactured, including the targets 50, the orthodontic appliances 90 are temporarily affixed to the tooth models 110 at positions provided by the targets 50, i.e. recesses 60, 160 and/or 260, via a weak adhesive, interference fit, and so on, optionally with a buffer layer, as already disclosed herein. The tray 200 may then be manufactured for example as in traditional indirect bonding techniques, comprising pressure or vacuum forming a suitable sheet material, such as 0.75 mm thermal forming dental material, over the model 100 and appliances 90. Suitable thermal forming dental materials may include, for example, biocryl, by Great Lakes Orthodontics Ltd., Tonawanda, N.Y.

Figure 6A:
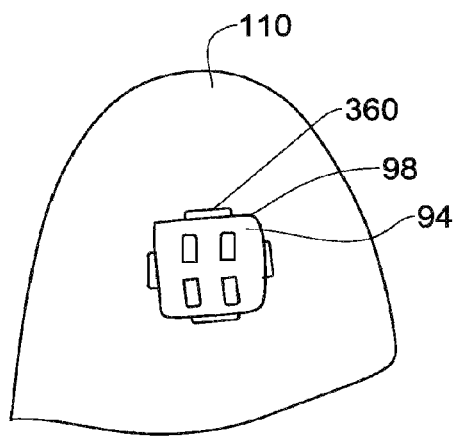
Figure 6B:
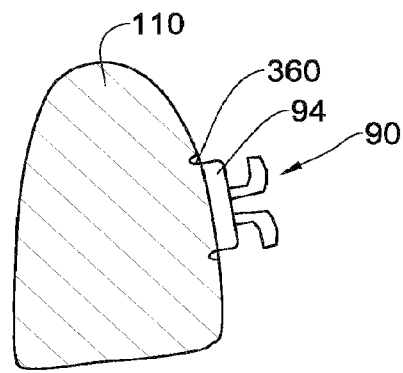

In a second embodiment of the invention, and referring to FIGS. 6a to 6b, the physical model 100' comprises all the elements and features of the first embodiment, as described herein mutatis mutandis, with the following differences. In the second embodiment, the targets 50 are configured to provide visual clues on the physical model 100' which enable the orthodontic appliances 90 to be located at the desired locations over the respective tooth model 110 of model 100 in the absence of any recessed mechanical structure or stops that are configured for defining the location of the appliance 90 by abutment therewith.

In the embodiment of FIGS. 6a and 6b, having chosen the particular orthodontic appliance 90 having a known shape for the base 94 thereof, a number of notches 360 are provided on the respective tooth model 110 of the model 100. The notches 360 coincide with parts of the periphery 98 of the base 94, enabling the base 94 to be visually aligned with the notches, thereby enabling the orthodontic appliance 90 to be navigated into its correct position, although the notches do not mechanically hold the appliance 90 in place with respect to any degree of freedom. As best seen in FIG. 6b, the notches 360 comprise a physical cut or an indentation into the surface of the tooth model 110.

Figure 6C:
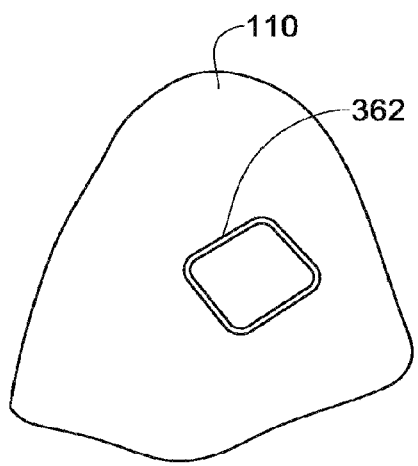

In a variation of this embodiment, and referring to FIG. 6c, the plurality of notches 360 of FIGS. 6a and 6b is replaced with single notch 362 that circumscribes the periphery 98 of base 94.

Figure 6D:
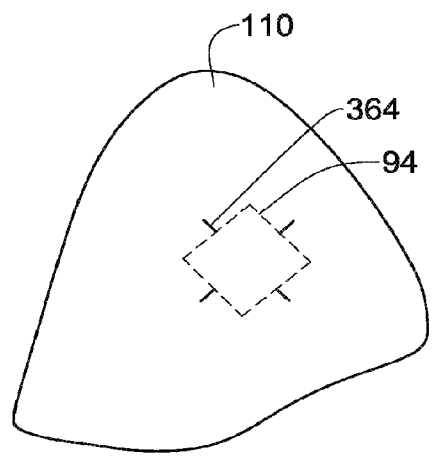

In another variation of this embodiment, and referring to FIG. 6d, the plurality of notches 360 of FIGS. 6a and 6b is replaced, or alternatively supplemented, with targeting marks 364 that help the user align the periphery 98 of base 94 in the desired location.

In yet another variation of this embodiment, and referring to FIGS. 6e and 6f, targeting marks 366 are engraved or otherwise formed on the surface of the tooth model 110, for example generally aligned in the occlusal direction, and these marks are to be aligned with reference marks 290 provided on the appliance 90. Thus, and as illustrated in FIG. 6f, when the targeting marks 366 and reference marks 290 are aligned, the appliance 90 is considered to be in the desired location on the tooth model. Of course, the targeting marks may be inclined at any angle with reference to the occlusal direction, and arranged in any desired manner on the tooth model 110, so long as this matched the corresponding marks on the appliance 90, such that aligning the targeting marks on the tooth model with the marks on the appliance positions the appliance on the model in a unique and repeatable manner.

As illustrated in FIG. 6h, the targeting marks 366 may be directly engraved into the surface of the model 110 to provide an indentation 368', or alternatively, as illustrated in FIG. 6g, the marks 366 may be formed as protruding structures 367 by removing material in the vicinity of the marks to provide a slight indentation 368 at least partially surrounding the protruding structures 367. However, it is to be noted that the surface of the indentation 368, or of indentation 368', is not considered a "dental surface" per se in the meaning of the present invention, as it does not correspond to a real dental surface of the real teeth.

Alternatively, the position of a datum with respect to each orthodontic appliance 90 may be marked on the respective tooth model 110, for example as a "+" or "X" symbol or mark, such that the center or other part of the mark corresponds to the center or other known location relative to the orthodontic appliance 90, respectively, and the orientation of the mark is indicative of the desired orientation of the orthodontic appliance 90, for example. Such a reference datum may be referred to a bracket centerline, bracket slot or any other convenient reference on the orthodontic appliance 90 by which it is possible to place the orthodontic appliance 90 in a desired position with some accuracy.

Thus, according to one aspect of the second embodiment, the targets 50 are in the form of a physical marking that is engraved, scratched or otherwise formed as a depression into the surface of the tooth model 100.

Alternatively, according to another aspect of the second embodiment, rather than providing a physical mark as an indentation into the surface of the physical model, the targets 50 in the second embodiment and variations thereof may be provided as optical marks, which are characterized as having a different color and/or contrast or other optical property with respect to the rest of the surface of the physical model 100, in particular the respective tooth model 110 thereof, without necessarily providing a physical mark that is engraved or otherwise physically projecting into the surface of the tooth model. Thus, such targets 50 can be printed, drawn, painted, colored or otherwise provided on the surface of the tooth model 110, similar to the notches and other physical markings of the embodiment of FIGS. 6a to 6d, mutatis mutandis, without the necessity of actually or effectively physically removing material with respect to the dental surfaces of the model 100.

In yet another variation of the second embodiment, the targets 50 are provided as visual clues that are slightly protruding from the original surface of the tooth model 110, though not sufficiently and/or in a configuration to provide a mechanical structure or stops that are configured for defining the location of the appliance 90 by abutment therewith.

The targets 50 in the form of notches 360, 362, 364, 366 etc, or corresponding optical markings can be provided in a similar manner to the recesses 60, 160 or 260 of the first embodiment, mutatis mutandis, with some differences, for example as follows.

Figure 8:
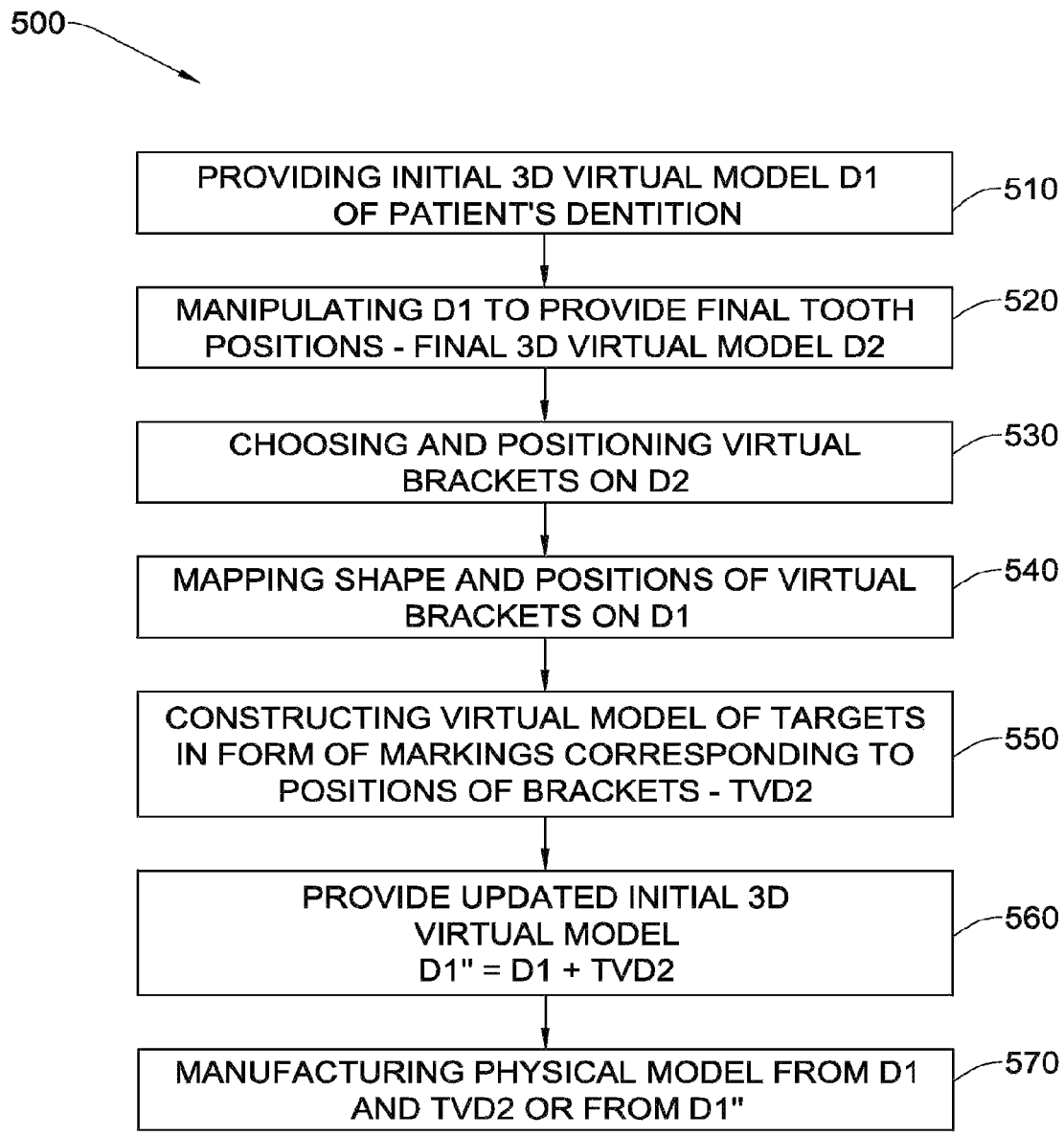
FIG. 8 illustrates general steps of another method for manufacturing the tooth model of FIG. 1 according to an embodiment of the invention.

Referring to FIG. 8, a 3D numerical model of the teeth is provided, and the three-dimensional positions of the brackets or other orthodontic appliances with respect to the 3D numerical model are defined, and the physical model according to the second embodiment or variations thereof is manufactured, according to method 500.

Method 500 comprises method steps 510, 520, 530, 540, which are substantially identical to method steps 410, 420, 430, 440, respectively of method 400 as disclosed herein, mutatis mutandis.

In the next step 550, virtual models of the targets 50 in the form of the positions and shapes of the virtual markings are created—collectively referred to as TVD2—based on the shapes and locations of the chosen orthodontic appliances 90.

In step 560, the initial virtual model D1 is updated to incorporate the virtual models TVD2 to create an updated initial virtual model D1″, in which the original virtual model D1 modified to integrally include the chosen markings in the positions corresponding to the chosen respective orthodontic appliances 90 instead of the original virtual tooth surfaces at those positions.

In the next step 570, the physical model 100 of the dentition including the targets according to the second embodiment or variations thereof is manufactured using computer controlled manufacturing methods, based on virtual models D1 and TVD2, or based on virtual model D1″.

Step 570 may be carried out in a number of ways, for example using material removal techniques, for example CNC machining methods, or other methods, such as for example rapid prototyping techniques.

Using CNC machining methods, the model 100 may be produced either indirectly or directly. Such indirect methods may comprise, e.g., manufacturing an appropriate female mold using CNC techniques, and then producing a model 100 from the mold using casting techniques. The female mold comprises an internal 3D structure substantially complementary to that defined by virtual model D1′, in which the locations and form of the markings are integrally and complementarily formed in the female mold as beads or the like, which form the required physical markings in the form of notches or the like indented into the surface of the cast model, when the targets 50 are chosen thus.

Alternatively, in direct CNC methods, a suitable CNC machine may be programmed to provide material removal passes over a blank of suitable material, based on dataset D1 or D1″, such as to manufacture the model 100. For example, the targets 50 in the form of the aforesaid physical markings indented into the model may be integrally formed with the model 100, wherein the model 100 is manufactured based on virtual model D1″. Alternatively, the targets 50 may be formed as a separated operation after the model 100 is produced based on virtual model D1, wherein the position and form of the targets 50 is post-machined based on target virtual model TVD2. For example, a sharp tool may be CNC controlled to provide the physical markings on the model. In the case where at least some of the targets 50 are the aforesaid optical markings, a tool comprising a pen, printer head or the like may be mounted onto a CNC controlled machine, and CNC controlled so as to print, draw or paint the optical markings at the required positions on the model 100.

Alternatively, the model 100 may be formed using other techniques such as for example from an impression of the intra-oral cavity, and the targets 50 in the form of physical markings or optical markings may be formed using CNC machining techniques based on target virtual model TVD2, as disclosed above, mutatis mutandis. In such a case, the spatial position and orientation of model 100 as a whole must be known with respect to a machining datum so that marking operations are applied to the desired parts of the model to form the physical or optical markings. Accordingly, it is possible to set the model 100 on a rig or chuck to hold the same in place, and thereafter scanned using a suitable 3D scanner to provide a virtual model of the physical model, to be followed by creation of the physical or optical markings based on target virtual model TVD2, which is manipulated to be in registry with the virtual model of the scanned physical model 100. Alternatively, the model 100 may be fabricated with indicia that help align the physical model 100 with respect to predetermined datums in the CNC machine, to which the target virtual model TVD2 is also referenced.

Alternatively, the model 100 is fabricated using other methods. For example, the model 100 may be fabricated using rapid prototyping techniques, for example based on a stereolithography machine, such as for example Model SLA-250/50 available from 3D System, Valencia, Calif., based on the virtual model D1. A liquid or non-hardened resin is hardened into a 3D form that can be separated from the non-hardened liquid or resin to form a positive model 100 from the 3D numerical model D1 thereof. Then, the targets 50 in the form of physical markings or optical markings may be formed in the model 100 in a similar manner to that described above, for example, mutatis mutandis, for example by CNC control.

Alternatively, the model 100 may be manufactured integrally with the targets 50 using rapid prototyping techniques based on virtual model D1", in a similar manner to that described above for virtual model D1', mutatis mutandis. Where the targets 50 comprise physical markings, the rapid prototyping method automatically creates the physical markings by providing an effective absence of material at the respective locations of the markings. Additionally or alternatively, where the targets 50 comprise optical markings, the stereolithography machine may be programmed to provide at the locations of the markings, resin having a different optical property to that of the resin used for rest of the model 100, at least when the resin hardens, so that the optical markings are visually marked on the model as lines or symbols and so on having a different optical property or characteristic—color, contrast, etc—to the rest of the model 100.

Once the model 100 is finished with the targets 50 in the form of the physical markings and/or the optical markings, the orthodontic appliances 90 are placed at the correct positions on model 100 as guided by the markings, and the transfer tray 200 may then be manufactured, for example as in traditional indirect bonding techniques, comprising pressure or vacuum forming a suitable sheet material, such as 0.75 mm thermal forming dental material. Suitable materials include, for example, biocryl, by Great Lakes Orthodontics Ltd., Tonawanda, N.Y.

Both for the first and second embodiments, the targets 50 may be created as a separate CNC controlled machining operation of the physical model 100, using any suitable tooth, such as for example a sharp or heated cutting tool, a laser or a power tool, marking tool, printing tool, and so on, as appropriate.

Thus, the targets 50 thus provided enable locations of orthodontic appliances 90 to be targeted, and for the orthodontic appliances 90 to be navigated, homed onto and placed at the desired areas of the physical tooth model 100, and thus also to be placed onto the desired areas of the patient's teeth by means of the transfer tray 200. Optionally, the model 100 may be suitably marked in the vicinity of each target 50 with an identifying mark, symbol or alphanumeric character, for example, that identifies the particular type of orthodontic appliance 90 that is supposed to be targeted onto and bonded to the particular tooth model 110 of the model 100 via that target 50. Such an identifier may be printed, etched or in any other manner provided on the model 100.

Thus, a suitable marking implement such as a pen, pencil, printing pad or the like, for example, may be used to mark the area, in ink for example, this mark delineating the position required for the orthodontic appliance 90, for each tooth.

The present invention may also be used for providing remedial assistance during an orthodontic procedure that is already under way. Such assistance may arise when a bracket or other orthodontic appliance falls off a tooth during the course of an orthodontic treatment, for example. Relative to the corresponding tooth, a particular bracket remains in the same position during the full duration of the orthodontic treatment. There are at least two ways of re-installing the missing bracket. According to one method, the original tooth model 100 may be used again to place the orthodontic appliance 90 on the particular tooth model 100 corresponding to the real tooth that is missing the orthodontic appliance 90. Then, a transfer tray for that tooth only is formed over the respective tooth model 110 and orthodontic appliance 90, and the orthodontic appliance 90 is transferred to the real tooth via indirect bonding using the single tooth transfer tray. Thus, even if the tooth has moved significantly since the orthodontic treatment started, since the relative position of the orthodontic appliance 90 with respect to the respective tooth is unchanged, the single tooth transfer tray provides an effective solution.

According to another embodiment of the method, an intermediate virtual model of the dentition can be created, in a similar manner to model 100, mutatis mutandis, taking into account the current positions of the teeth at the intermediate point of the orthodontic treatment. Then, the virtual model corresponding to the target 50 of the particular tooth, for example part of TVD1 or of TVD2, is incorporated into this intermediate virtual model, and a corresponding intermediate physical model can be manufactured together with the target 50 on the aforesaid tooth model 110. The orthodontic appliance 90 is then placed on the particular tooth model 110 corresponding to the real tooth that is missing the orthodontic appliance 90 using the respective target 50. Then, a transfer tray for the full model 100 is made, affixing thereto orthodontic appliance 90, which is transferred to the real tooth via indirect bonding using the transfer tray.

Thus, it may be desired to change the relative position of the orthodontic appliance 90 with respect to the respective tooth, and thus the procedure may be used for providing remedial assistance, or for adjusting an orthodontic treatment by changing the position of the bracket during treatment.

In another variation of the second embodiment, the optical markings are in the form of a transfer patch of a suitable material that is transferred to the respective tooth model. The transfer patch may comprise an adhesive label, for example, that is transferred to the tooth model 110. The adhesive label may be, for example, in the shape of the periphery of the required orthodontic appliance 90, so that the orthodontic appliance 90 may be fitted in the open area in the patch after the patch is adhered to the tooth model.

Alternatively, the patch may cover part or all of the target area, and the orthodontic appliance 90 is fitted onto the patch. The adhesive patch may comprise a chemical or light-cured adhesive, which sets when the patch has been properly seated and aligned on the tooth model 110. Optionally, the patch may comprise adhesive on both sides thereof, enabling the patch to first bond onto the tooth model 110, and then allow the orthodontic appliance 90 to be bonded to the patch. Accordingly, it may be convenient to have different adhesives for each of the sides of the patch, and such that each adhesive may be selectively activated independently of the other. For example, the adhesives may be light-curing adhesives, each of which cures at a different wavelength. This facilitates the procedure of bonding the patch to the tooth model first, and then allowing the orthodontic appliance 90 to be bonded to the patch. Optionally, the patch may be in the form or shape of the bracket, or in any other suitable shape such as to guide the bracket to the required alignment with respect thereto and thus the tooth model.

Once the shape and dimensions of the patch, and their relationship to the position and orientation of the respective orthodontic appliance 90 on the respective tooth model 110, a suitable robot or robotic arm may be suitably programmed, based on the aforementioned virtual models of the intraoral cavity and of the targets, to place the patch at the desired location over the model 110.

Thus, the physical or optical markings according to the second embodiment provide sufficient targeting information for each orthodontic appliance 90, which may be positioned and bonded onto the appropriate part of the tooth model 110 by placing and aligning the orthodontic appliance 90 in registry with the corresponding mark.

The second embodiment also allows the choice of actual bracket to be deferred if desired or necessary, for example due to logistical problems in obtaining specific types of brackets. Since the positional data required for the orthodontic appliance 90 is marked on the model 100, it is possible to target any orthodontic appliance 90 to a particular target 50, so long as the orthodontic appliance 90 comprises suitable datums compatible with the marking criteria used for the marking, for example centerline and slot location datums.

In a third embodiment of the invention, the physical model 100 comprises the elements and features of the first and second embodiments, as described herein, mutatis mutandis, in which at least one target 50 is configured to provide visual clues which enable the orthodontic appliances 90 to be located at the desired locations over the respective tooth model 110" of model 100", and also provides at least one mechanical stop to define the location with respect to at least one axis or degree of freedom by abutment therewith. Thus referring to FIGS. 9a to 9d, the target 50 according to the third embodiment comprises a ledge-shaped recess 600 formed into the material of the tooth model 110, comprising a shoulder 620 and a base 610. The shoulder 620 and base provide abutments for an edge 92 the underside, respectively, of the base element 94 of an orthodontic appliance 90. In this embodiment, the orthodontic appliance 90 can slide in the direction marked 625 along the edge between the shoulder 620 and base 610, and the desired position of the orthodontic appliance 90 along this direction is provided by optical marks, similar to those of the second embodiment, for example a peripheral mark 630 corresponding to the perimeter of the base 94, and/or datum marks 640 corresponding to the mid-point and/or corners of the side 92 that is in abutment with the shoulder 620. The model 100 comprising recess 600 can be manufactured using a combination of techniques already described for the first and second embodiments, mutatis mutandis, and where the recess 600 is provided as a post-machining operation on a prepared model 100, such a post-machining operation is relatively simple, as it may comprise effectively cutting a slice with a wedge-shaped cross-section off from the respective tooth model.

In a variation of the third embodiment, and referring to FIGS. 10a to 10d, recess 700 comprises all the elements and features of recess 600 of the embodiment of FIGS. 9a to 9d, with the following differences. In the embodiment of FIGS. 10a to 10d, the recess 700 has a shoulder 720 and base 710, rather than providing visual or physical clues for aligning the orthodontic appliance 90 along direction 625, a mechanical stop 750 is provided, protruding from the base 710, and an edge 92a adjacent to edge 92 is abutted onto the stop 750, thereby constraining the orthodontic appliance 90 onto the tooth model 110 in all degrees of freedom. It is to be noted that in this embodiment, stop 750 has height, width and depths dimensions that are within the envelope defined by the imaginary surface 117 of the tooth model 110 that was removed to form the recess base 710 and shoulder 720. Thus, for example, the stop 750 may be manufactured in a machine removal operation while making the recess 700. Furthermore, it is also to be noted that the surface of the recess base 710 is not considered a "dental surface" per se in the meaning of the present invention, as it does not correspond to a real dental surface of the real teeth.

In a variation of the embodiment of FIGS. 10a to 10d, the stop 750 may comprise a separate component that is mounted in place on base 710 after this is cut out or otherwise formed on the tooth model 110. The stop 750 is thus manufactured separately to the model 100. When making the recess 700, a suitable hole (not shown) may be drilled or otherwise formed on base 710, and the stop 750 comprises a projection to enable the stop 750 to be positioned accurately on the base 710.

In yet other embodiments of the invention, the model 100 may comprise any combination and permutation of targets 50 according to the first embodiment, and/of the targets 50 according to the second embodiment, and/or the targets 50 according to the third embodiment, mutatis mutandis.

Optionally, the model 100 according to any of the embodiments or variations thereof, may be fabricated at one location, and then transported to another location where the targets 50 are formed. Alternatively, the model 100 including targets 50 may be fabricated at a single location. Further optionally, placement of the orthodontic appliances 90 on the model 100, and/or formation of the tray 200, may be performed at the same location, or at a different location to that used for manufacturing the model 100 and/or the targets 50.

For at least the embodiments or variations thereof disclosed herein, it is possible optionally and additionally to mark the physical model with useful information including, for example, at least one of: the name of the patient; the name of the orthodontist; the name of the dental lab that manufactured the tray; the date of manufacture; the model, type, serial numbers, or other identifying references for the brackets; and so on.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

What is claimed is:

1. A dental model for facilitating placement of an orthodontic appliance at a desired location, the model comprising:
   a positive physical model of at least a portion of a patient's dentition, the positive physical model comprising at least one target, the at least one target comprising a recessed mechanical stop shaped to receive at least a portion of the orthodontic appliance and constrain movement thereof without a need for an adhesive in order to facilitate the placement of the orthodontic appliance at the desired location on the positive physical model.

2. The dental model of claim 1, wherein the positive physical model comprises a model dental surface corresponding to a real dental surface of the patient's dentition.

3. The dental model of claim 2, wherein the recessed mechanical stop projects into the model dental surface.

4. The dental model of claim 1, wherein the recessed mechanical stop is shaped to receive a perimeter edge of the orthodontic appliance.

5. The dental model of claim 1, wherein the recessed mechanical stop comprises at least one recess edge to which at least one perimeter edge of the orthodontic appliance is abutted to constrain the movement of the orthodontic appliance.

6. The dental model of claim 1, wherein the at least one target further comprises one or more markings providing visual targeting information to facilitate the placement of the orthodontic appliance at the desired location on the positive physical model.

7. A method for manufacturing a dental model for facilitating placement of an orthodontic appliance at a desired location, the method comprising:
forming a positive physical model of at least a portion of the patient's dentition; and
forming at least one target in the positive physical model, the at least one target comprising a recessed mechanical stop shaped to receive at least a portion of the orthodontic appliance and constrain movement thereof without a need for an adhesive in order to facilitate the placement of the orthodontic appliance at the desired location on the positive physical model.

8. The method of claim 7, further comprising positioning the orthodontic appliance at the desired location on the positive physical model using the at least one target.

9. The method of claim 8, further comprising:
positioning a transfer tray over the positive physical model so as to embed the orthodontic appliance into the transfer tray;
removing the transfer tray and the orthodontic appliance embedded therewithin from the positive physical model; and
positioning the transfer tray over the patient's dentition so as to transfer the orthodontic appliance to the patient's dentition at a desired location corresponding to the desired location on the positive physical model.

10. The method of claim 7, wherein the orthodontic appliance comprises a buffer layer and the recessed mechanical stop is shaped to receive the buffer layer.

11. The method of claim 10, wherein the orthodontic appliance comprises an appliance base and the buffer layer is removably attached to the appliance base.

12. A system for manufacturing a dental model for facilitating placement of an orthodontic appliance at a desired location, the system comprising:
a computer controlled manufacturing center configured to,
form a positive physical model of at least a portion of the patient's dentition, and
form at least one target in the positive physical model, the at least one target comprising a recessed mechanical stop shaped to receive at least a portion of the orthodontic appliance and constrain movement thereof without a need for an adhesive in order to facilitate the placement of the orthodontic appliance at the desired location on the positive physical model.

13. The system of claim 12, wherein the computer controlled manufacturing center is configured to form the positive physical model and the at least one target in the positive physical model using at least one of a CNC machining process or a rapid prototyping process.

14. The system of claim 12, wherein the computer controlled manufacturing center is configured to form the at least one target in the positive physical model concurrently while forming the positive physical model.

15. The system of claim 12, wherein the computer controlled manufacturing center is configured to form the at least one target in the positive physical model after forming the positive physical model.

16. The system of claim 12, wherein the computer controlled manufacturing center is configured to form the positive physical model and the at least one target in the positive physical model based on one or more virtual models of the positive physical model and the at least one target.

* * * * *